(12) United States Patent
Greist

(10) Patent No.: US 10,449,266 B2
(45) Date of Patent: Oct. 22, 2019

(54) SYSTEMS AND METHODS FOR FABRICATING AN AIR PURIFICATION DEVICE

(71) Applicant: Lennox Industries Inc., Richardson, TX (US)

(72) Inventor: Henry Todd Greist, Gainesville, FL (US)

(73) Assignee: Lennox Industries Inc., Richardson, TX (US)

( * ) Notice: Subject to any disclaimer, the term of this patent is extended or adjusted under 35 U.S.C. 154(b) by 153 days.

(21) Appl. No.: 15/447,082

(22) Filed: Mar. 1, 2017

(65) Prior Publication Data

US 2017/0173205 A1    Jun. 22, 2017

Related U.S. Application Data

(62) Division of application No. 14/798,390, filed on Jul. 13, 2015, now Pat. No. 9,623,139.

(60) Provisional application No. 62/155,434, filed on Apr. 30, 2015.

(51) Int. Cl.
  *A61L 9/20* (2006.01)
  *B01J 35/00* (2006.01)
  *B01J 35/04* (2006.01)

(52) U.S. Cl.
  CPC .............. *A61L 9/205* (2013.01); *B01J 35/004* (2013.01); *B01J 35/04* (2013.01); *A61L 2209/16* (2013.01)

(58) Field of Classification Search
  CPC .... B01D 46/0001; B01D 46/00; B01D 46/24; B01D 46/2418
  See application file for complete search history.

(56) References Cited

U.S. PATENT DOCUMENTS 4,981,744 A * 1/1991 Swank ...................... B32B 7/14
                                                        428/116
2004/0241040 A1* 12/2004 Wei ..................... B01D 53/8668
                                                         422/4

* cited by examiner

*Primary Examiner* — Kelly M Gambetta
(74) *Attorney, Agent, or Firm* — Hubbard Johnston, PLLC

(57) ABSTRACT

Systems and methods for fabricating an air purification device for use typically with heating, ventilating, and air conditioning (HVAC) system are presented. The systems include at least one pleated insert disposed within a cartridge housing and proximate a source of electromagnetic radiation. The pleated insert includes a plurality of pleat strips aligned substantially parallel to a common pleat axis. Each pleat strip has a first edge and a second edge. Portions or surfaces proximate the first edge and the second edge of each pleat strip are bonded so as to form an alternating sequence of peaks and valleys. A photocatalytic material coats at least a portion of the pleated insert. Methods for fabricating the pleated insert from a slice member having an unexpanded honeycomb structure are also presented. Other systems and methods are presented.

10 Claims, 7 Drawing Sheets

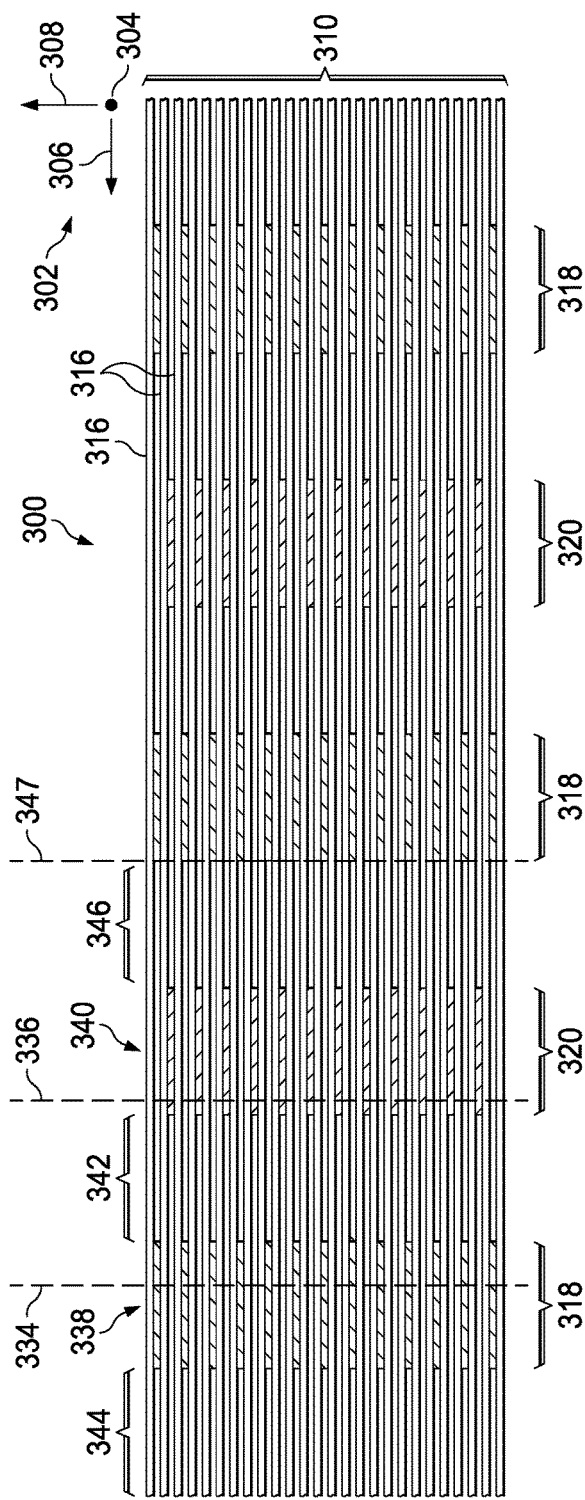
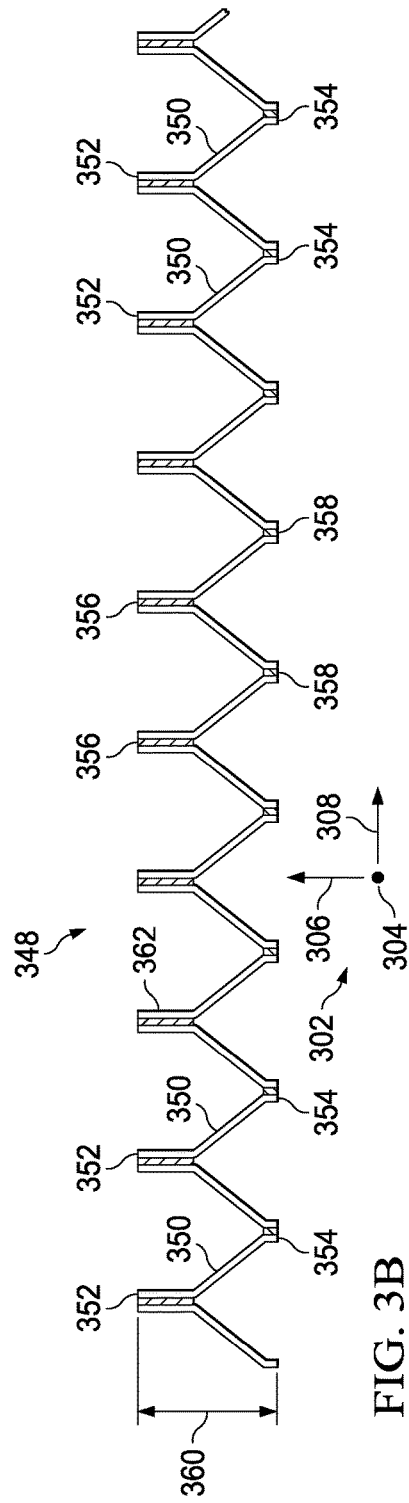
FIG. 3A
FIG. 3B

SYSTEMS AND METHODS FOR FABRICATING AN AIR PURIFICATION DEVICE

RELATED APPLICATIONS

This application is a Divisional of U.S. application Ser. No. 14/798,390 filed Jul. 13, 2015, which claims the benefit of U.S. Provisional Application No. 62/155,434 filed Apr. 30, 2015, both of which are incorporated herein by reference for all purposes.

TECHNICAL FIELD

The present disclosure relates generally to systems and methods for fabricating an air purification device for use typically with a heating, ventilating, and air conditioning (HVAC) system.

BACKGROUND

Some air purification systems incorporated into HVAC systems utilize a photocatalytic oxidation (PCO) process or other catalytic process. The PCO process uses ultraviolet light (UV) and airborne water vapor to activate a catalyst, typically titanium dioxide. The activated catalyst generates hydroxyl radicals. The hydroxyl radicals break down contaminants in the air, such as odors, chemicals, and other organic compounds into less harmful substances, such as carbon dioxide and water. Other filtering approaches may be used.

SUMMARY

According to an aspect of the disclosure, methods and systems are included that covert unexpanded honeycomb slices into pleated strips that can be coated and used in a photocatalytic oxidation (PCO) process or other catalytic process.

According to an illustrative embodiment, a method for fabricating a pleated substrate for use in an HVAC catalytic air filter from a slice member having an unexpanded honeycomb structure includes making a first cut through the slice member, the first cut substantially parallel to a longitudinal axis of the unexpanded honeycomb structure and in a vertical plane and making a second cut through the slice member, the second cut laterally displaced from the first cut and substantially parallel thereto, the second cut to produce a slice section. The method further includes stretching the slice section in an expansion direction to a predetermined length in order to form the pleated substrate. The first cut is through a first column of unexpanded honeycomb cells in the unexpanded honeycomb structure. The second cut is through a second column of unexpanded honeycomb cells in the unexpanded honeycomb structure wherein the second column of unexpanded honeycomb cells is adjacent the first column of unexpanded honeycomb cells. The method may also include coating the pleated substrate with a photocatalytic material to form a pleated insert. The method may further include disposing the pleated insert into a housing having a source of electromagnetic radiation and configured to purify air.

In the method of the previous paragraph the slice member may comprise a plurality of strips arranged in a stack. The adjacent strips in the plurality of strips are alternately joined by a first series of spaced bonds and a second series of spaced bonds. The first series of spaced bonds and the second series of spaced bonds are aligned substantially parallel to the longitudinal axis of the unexpanded honeycomb structure. The second series of spaced bonds is displaced laterally relative to the first series of spaced bonds so that the slice member, upon expansion, assumes a slice member structure having a honeycomb cross-section.

The method may further include producing the slice member by cutting through a preform having the unexpanded honeycomb structure, the cutting substantially perpendicular to the longitudinal axis of the unexpanded honeycomb structure. The preform is comprised of a plurality of sheets arranged in a stack. Adjacent sheets in the plurality of sheets are alternately joined by a first series of spaced longitudinal bonds and a second series of spaced longitudinal bonds. The first series of spaced longitudinal bonds and the second series of spaced longitudinal bonds aligned substantially parallel to the longitudinal axis of the unexpanded honeycomb structure. The second series of spaced longitudinal bonds is displaced laterally relative to the first series of spaced longitudinal bonds so that the preform, upon expansion, assumes a preform structure having the honeycomb cross-section. Other variations are possible.

According to another illustrative embodiment, a system for purifying air using electromagnetic radiation includes a cartridge housing; a source of electromagnetic radiation disposed within the cartridge housing; and at least one pleated insert disposed within the cartridge housing and proximate the source of electromagnetic radiation. The at least one pleated insert includes a plurality of pleat strips aligned substantially parallel to a common pleat axis, each pleat strip having a first edge and a second edge. Surfaces proximate the first edge and the second edge of each pleat strip are bonded to adjacent pleat strips so as to form an alternating sequence of peaks and valleys. A photocatalytic material coats at least a portion of the pleated insert. The cartridge housing is configured to guide air to the at least one pleated insert. The at least one pleated insert may comprise two pleated inserts with the two pleated inserts positioned opposite each other so as to straddle the source of electromagnetic radiation.

According to still another illustrative embodiment, a method for fabricating a pleated substrate from a slice member having an unexpanded honeycomb structure includes making a first cut through the slice member, the first cut substantially parallel to a longitudinal axis of the unexpanded honeycomb structure and in a vertical plane; making a second cut through the slice member, the second cut laterally displaced from the first cut and substantially parallel thereto, the second cut to produce a slice section; and stretching the slice section to a predetermined length to form the pleated substrate. The first cut is exclusively through a first column of unexpanded honeycomb cells in the unexpanded honeycomb structure. The second cut is exclusively through a second column of unexpanded honeycomb cells in the unexpanded honeycomb structure. The second column of unexpanded honeycomb cells is adjacent the first column of unexpanded honeycomb cells. The method may further include coating the pleated substrate with a photocatalytic material to form a pleated insert.

A number of advantages may be realized from the disclosed embodiments. For example, without limitation, a high surface structure may be formed that allows for enhanced exposure to a photocatalytic material in some embodiments or a use in a more confined space. As another non-limiting example, the pleated substrates herein may be produced without requiring a mechanical pleater. As still another non-limiting example, an embodiment of the present disclosure may facilitate multiple pleat heights, pleat shapes, and pleat densities.

BRIEF DESCRIPTION OF THE DRAWINGS

Illustrative embodiments of the present disclosure are described in detail below with reference to the attached drawing figures, which are incorporated by reference herein.

FIG. 3A is a front elevation view of a slice member having an unexpanded honeycomb structure, according to an illustrative embodiment;

FIG. 3B is a front elevation view of a pleated substrate fabricated from the slice member of FIG. 3A, according to an illustrative embodiment;

Figure 1:
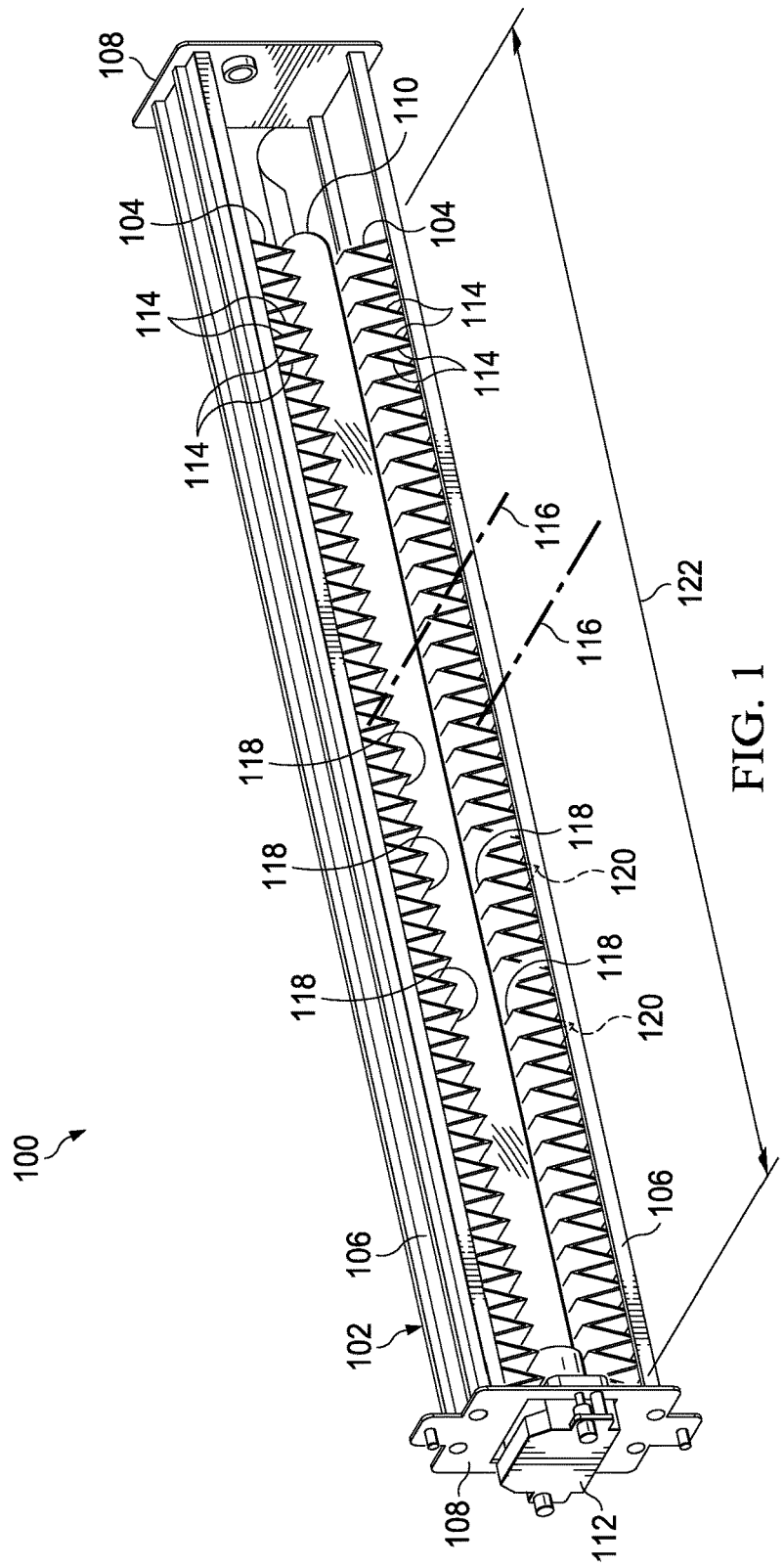
FIG. 1 is a perspective view of a system for purifying air using electromagnetic radiation, according to an illustrative embodiment.

The figures described above are only exemplary and their illustration is not intended to assert or imply any limitation with regard to the environment, architecture, design, configuration, method, or process in which different embodiments may be implemented.

DETAILED DESCRIPTION OF THE ILLUSTRATIVE EMBODIMENTS

In an air handling subsystem of a heating, ventilation, and air conditioning (HVAC) system, an intake air is often processed by an air purification unit that includes one or more particulate filters. Such particulate filters remove airborne pollutants from the intake air (e.g., dust, pollen, smoke, etc.) that would otherwise impart negative characteristics to a return air leaving the air handling subsystem (e.g., poor breathability). The air purification unit may also include an air purification device that breaks down pollutants in the intake air via photocatalytic oxidation (PCO).

In photocatalytic oxidation, hydroxyl radicals or ions are produced from moisture using ultraviolet light. More specifically, a photocatalytic material, commonly titanium dioxide, is energized by ultraviolet light, enabling electrons to transfer to moisture in the intake air. Such transfer produces hydroxyl radicals via ionization. These hydroxyl radicals or ions react with contaminants in the intake air (e.g., odors, chemicals, volatile organic compounds, etc.) to produce less harmful substances, typically carbon dioxide and water. Thus, the intake air, when processed additionally via photocatalytic oxidation, can exit the air purification unit as more purified than if particulate filters are used alone.

Approaches to constructing the air purification device typically involve incorporating a planar honeycomb structure that serves as a substrate for the photocatalytic material. In standard configurations, the planar honeycomb structure sits proximate a source of ultraviolet light (e.g., a linear lamp). Planar honeycomb structures are readily available in a variety of commercially produced preforms. However, the planar honeycomb structure is poorly suited for receiving light on its interior surfaces: cells within the honeycomb structure are prone to shadowing that reduces an intensity of ultraviolet light absorbed by the photocatalytic material. Using multiple sources of ultraviolet light may mitigate such shadowing. However, the incorporation of multiple sources of ultraviolet light into the air purification device increases cost and electrical complexity, both undesirable by-products.

The embodiments described herein relate to systems and methods for fabricating an air purification device for use typically with a heating, ventilating, and air conditioning (HVAC) system. The systems include at least one pleated insert disposed within a cartridge housing and proximate a source of electromagnetic radiation. The pleated insert includes a plurality of pleat strips aligned substantially parallel to a common pleat axis. Each pleat strip has a first edge and a second edge. Portions or surfaces proximate the first edge and the second edge of each pleat strip are bonded so as to form an alternating sequence of peaks and valleys. The alternating sequence of peaks and valleys enables an orientation of individual pleat strips, relative to the source of electromagnetic radiation, that allows electromagnetic radiation to be received directly onto the pleated insert with minimal shadowing. A photocatalytic material coats at least a portion of the pleated insert. Methods for fabricating the pleated insert from a slice member having an unexpanded honeycomb structure are also presented. Other systems and methods are presented.

Referring now to the drawings and primarily to FIG. 1, a perspective view is presented of a system 100 for purifying air using electromagnetic radiation, according to an illustrative embodiment. The system 100 may be incorporated into an HVAC system, e.g., as part of a return air duct or other location. The system 100 includes a cartridge housing 102 and at least one pleated insert 104 disposed within the cartridge housing 102. In some embodiments, such as that depicted in FIG. 1, the cartridge housing 102 may include longitudinal panels 106 and end plates 108. The cartridge housing is configured to guide air to the at least one pleated insert 104, which typically involves receiving air from the HVAC system and passing such air past the at least one pleated insert 104.

The system 100 also includes a source of electromagnetic radiation 110 disposed within the cartridge housing 102. The at least one pleated insert 104 is proximate the source of electromagnetic radiation 110. An electrical box 112 may be associated with an end plate 108 and electrically coupled to the electromagnetic radiation source 110. The source of electromagnetic radiation 110 may be an incandescent lamp, a fluorescent lamp, an LED, or any combination thereof. The source of electromagnetic radiation 110 may also include a plurality of such lamps (e.g., a strip of LEDs). Other sources of electromagnetic radiation 110 are possible.

The at least one pleated insert 104 includes a plurality of pleat strips 114 aligned substantially parallel to a common pleat axis 116 for each pleated insert 104. The common pleat axis 116 is characteristic of parallel folds or pleats along the at least one pleated insert 104. Each pleat strip 114 has a first edge 118 and a second edge 120. The first edge 118 and the second edge 120 are displaced from each other and reside on opposite sides of each pleat strip 114. Portions or surfaces proximate the first edge 118 and the second edge 120 of each pleat strip 114 are bonded to adjacent pleat strips so as to form an alternating sequence of peaks and valleys. Aspects of the at least one pleated insert 104 are described further in relation to FIGS. 3A and 3B. The at least one pleated insert 104 includes a photocatalytic material coating at least a portion thereof. The photocatalytic material may be a titanium oxide material or other suitable material. In some embodiments, such as that shown in FIG. 1, the system 100 includes two pleated inserts 104. In these embodiments, the two pleated inserts 104 are positioned opposite each other so as to straddle the source of electromagnetic radiation 110. In general, however, the alternating sequence of peaks and valleys enables an orientation of individual pleat strips 114, relative to the source of electromagnetic radiation 110, that allows electromagnetic radiation to be received directly onto the at least one pleated insert 104 with minimal shadowing.

In some embodiments, the source of electromagnetic radiation 110 is configured to extend along an expansion length 122 of the at least one pleated insert 104. The expansion length 122 is described further in relation to FIGS. 3A and 3B. In some embodiments, the source of electromagnetic radiation 110 is configured to emit ultraviolet radiation in a UVA frequency spectrum, a UVB frequency spectrum, a UVC frequency spectrum, or any combination thereof. In some embodiments, the source of electromagnetic radiation 110 is configured to extend along the expansion length 122 of the at least one pleated insert 104.

In some embodiments, the plurality of pleated strips 114 are bonded using an adhesive. In some embodiments, the plurality of pleated strips 114 includes an aluminum material. In some embodiments, the plurality of pleated strips 114 includes a kraft paper material. In some embodiments, the plurality of pleated strips 114 includes an aramid material. In general, the pleated strips 114 should provide adequate strength to serve as a carrier for a catalyst that interacts with electromagnetic radiation 110. Such strength should also be sufficient to maintain a shape of the at least one pleated insert 104 when air contacts the catalyst or pleated strips 114.

In operation, the source of electromagnetic radiation 110 emits photons that travel towards the at least one pleated insert 104. The photocatalytic material on the at least one pleated insert 104 absorbs such photons and becomes energized. Concomitantly, the cartridge housing 102 guides air delivered by the HVAC system between the source of electromagnetic radiation 110 and the at least one pleated insert 104. This air flows between pleats of the plurality of pleat strips 114 and in a direction substantially parallel to the common pleat axis 116. As a result, electrons are transferred from the energized photocatalytic material to air flowing nearby, forming an ionized air. The ionized air breaks down pollutants therein, producing a purified air that exits the cartridge housing 102.

Attention will now be directed to forming the plurality of pleated strips 114 or the at least one pleated insert 104. The process of forming the plurality of pleated strips 114, in one embodiment, includes using a slice member, as in FIGS. 2A-2C, and then using other steps to modify the slice member to form the plurality of pleated strips 144 (or the at least one pleated insert 104), as shown in subsequent figures.

Figure 2A:
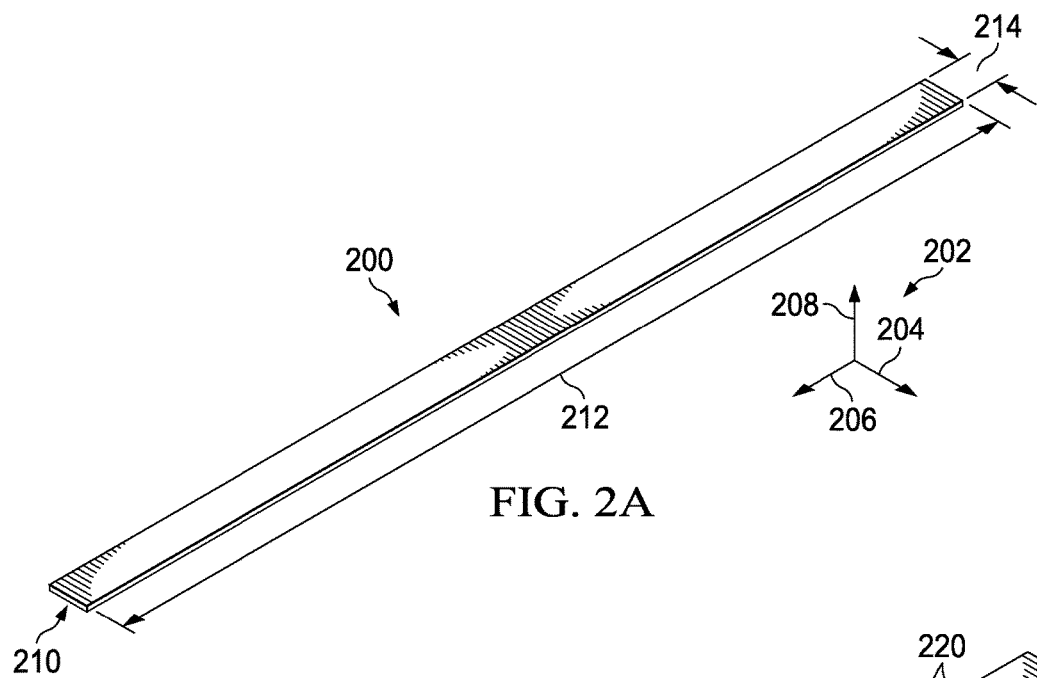
FIG. 2A is a perspective view of a slice member having an unexpanded honeycomb structure, according to an illustrative embodiment.

Referring now primarily to FIG. 2A, a perspective view is presented of a slice member 200 having an unexpanded honeycomb structure, according to an illustrative embodiment. The perspective view is shown in the context of individual axes 202 having a longitudinal direction 204, a lateral direction 206, and a vertical direction (or Z direction) 208. The individual axes 202, or reference axes, are orthogonal in configuration. The slice member 200 includes a plurality of strips 210 (see also FIG. 2B) arranged in a stack. In the plurality of strips 210, each strip shares a common width 212 and a common length 214. The common width 212 and the common length 214 run parallel to, respectively, the lateral direction 206 and the longitudinal direction 204.

Figure 2B:
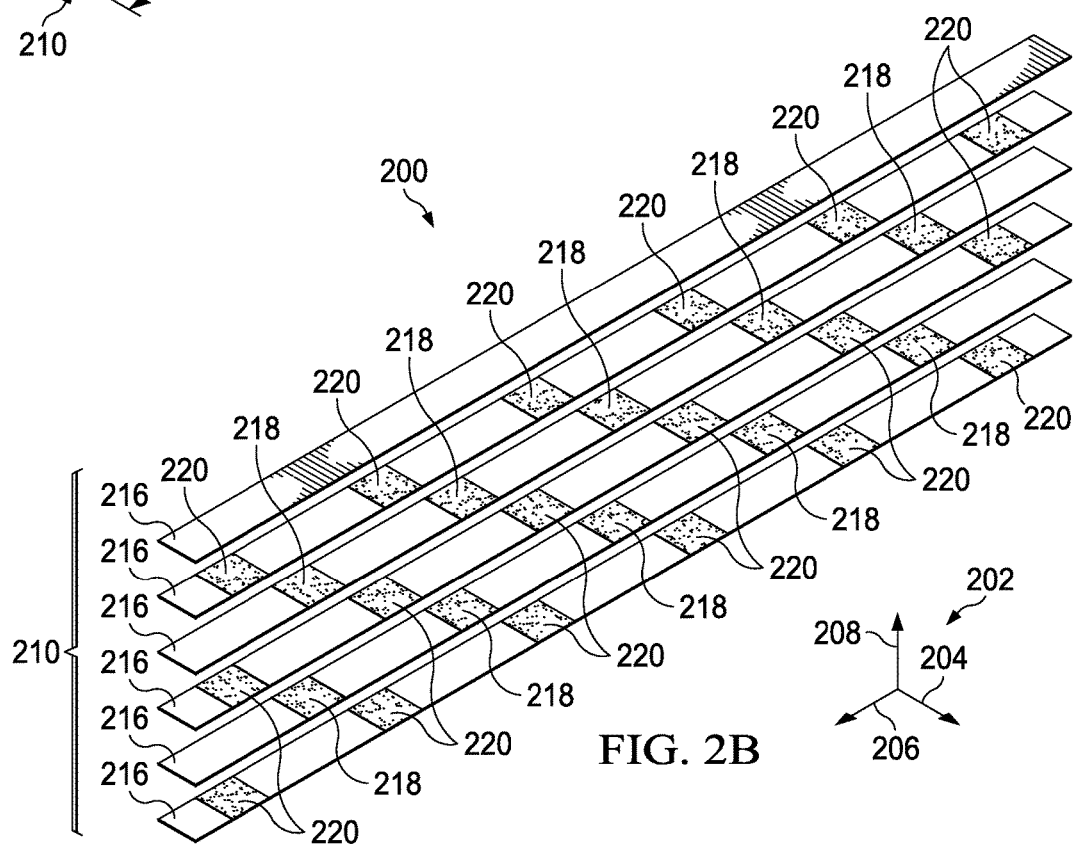
FIG. 2B is an exploded view of the slice member of FIG. 2A.

Now referring primarily to FIG. 2B, an exploded view is presented of the slice member 200 of FIG. 2A, according to an illustrative embodiment. Individual strips 216 in the plurality of strips 210 are shown with their corresponding regions of bonding 218, 220, which are aligned substantially parallel to the longitudinal direction 204. As will be described in relation to FIG. 2C, such regions of bonding 218, 220 enable the slice member 200, upon expansion, if not cut, to assume a structure having a honeycomb cross-section. The regions of bonding 218, 220 include a first series of spaced bonds 218 and a second series of spaced bonds 220. Relative to the first series of spaced bonds 218, the second series of spaced bonds 220 is displaced laterally, i.e., along the lateral direction 206. Adjacent strips 216 are alternately joined by the first series of spaced bonds 218 and the second series of spaced bonds 220. The first series of spaced bonds 218 and the second series of spaced bonds 220 may be formed by soldering, brazing, welding, ultrasonic welding, gluing, epoxying, adhesive bonding, or any other means of joining surfaces or bodies.

Figure 2C:
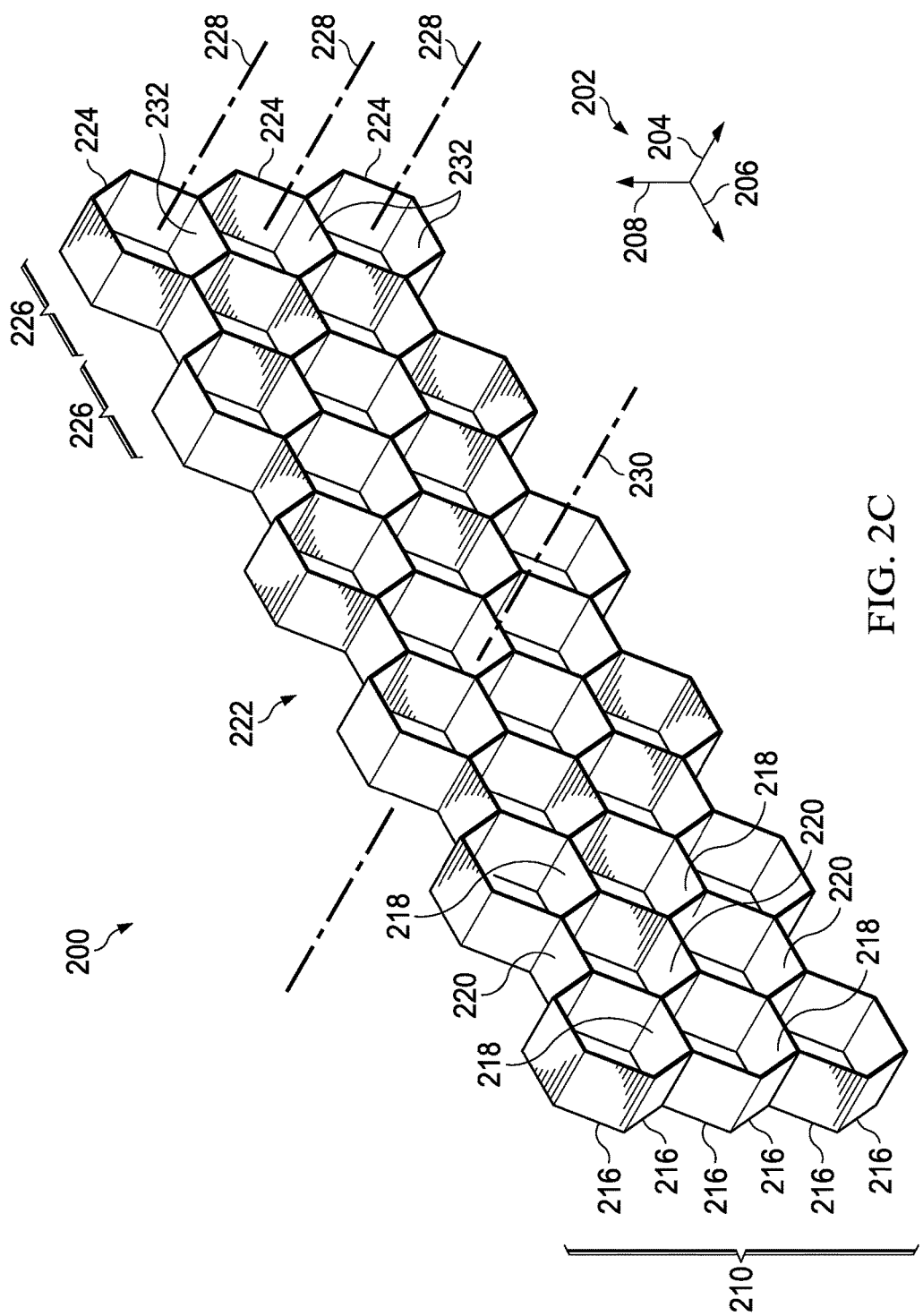
FIG. 2C is a perspective view of the slice member of FIG. 2A expanded into a structure having a honeycomb cross-section, according to an illustrative embodiment.

Now referring to FIG. 2C, a perspective view is presented of the slice member 200 of FIGS. 2A and 2B expanded into the structure having the honeycomb cross-section 222, according to an illustrative embodiment. For purposes of clarity, representative features of the slice member 200 may be identified in FIG. 2C when multiple instances are depicted. The honeycomb cross-section 222 corresponds to an interconnected network of honeycomb cells 224 that includes columns 226 of honeycomb cells 224 aligned in the vertical direction 208 (i.e., for the orientation shown). Each honeycomb cell 224 has a cell axis 228 that is coincident or parallel with a longitudinal axis 230 of the honeycomb cross-section 222. The longitudinal axis 230 of the honeycomb cross-section 222 is aligned parallel to the longitudinal direction 204. The honeycomb cross-section 222 includes nodes 232 that are parallel to a plane containing the longitudinal direction 204 and the lateral direction 206. The nodes 232 run parallel to the longitudinal axis 230 of the honeycomb cross-section 222 and have a node width approximately equal to a side length of the honeycomb cells 224. It will be appreciated that the nodes 232 occur in regions of contact between the plurality of strips 210. Thus, the nodes 232 define areas of bonding for the first series of spaced bonds 218 and the second series of spaced bonds 220. Although shown explicitly in FIG. 2C, the nodes 232 are also present in FIG. 2A by virtue of the first series of spaced bonds 218 and the second series of spaced bonds 220, which are present (but hidden) between adjacent strips 216 in the plurality of strips 210.

To ensure that the slice member 200 properly assumes the honeycomb cross-section 222 during expansion, i.e., transitions properly from an initial state shown in FIG. 2A to a final state shown in FIG. 2C, the nodes 232 are spaced using a predetermined interval. The predetermined interval, as measured along the length 212 of an individual strip 216, is approximately three times the side length of the honeycomb cells 224. Both the first series of spaced bonds 218 and the second series of spaced bonds 220 utilize the predetermined interval for spacing. However, relative to the first series of spaced bonds 218, the second series of spaced bonds 220 is offset approximately two side lengths along the lateral direction 206 (see FIG. 2B). During expansion from the initial state, the plurality of strips 210 (see FIG. 2A) translate along the vertical direction 208 thereby displacing the nodes 232. The final state is achieved when the structure having the honeycomb cross-section 222 contains cells exhibiting a virtually ideal hexagonal shape.

Although FIGS. 2A-2C depict the slice member 200 as having six strips 216, this depiction is not intended as limiting. Different numbers of strips 216 are possible for the slice member 200. Moreover, other parameters of the slice member 200 may be varied and still remain within the scope of the present disclosure. For example, and without limitation, such parameters may include the length 212, the width 214, the node width, and the predetermined interval. Other parameters are possible.

Now referring primarily to FIG. 3A, a front elevation view is presented of a slice member 300 having an unexpanded honeycomb structure, according to an illustrative embodiment. The slice member 300 of FIG. 3A is analogous to the slice member 200 shown in FIGS. 2A-2C. Features analogous to both FIG. 3A and FIGS. 2A-2C are related via coordinated numerals that differ in increment by a hundred. For purposes of clarity, representative features of the slice member 300 may be identified in FIG. 3A when multiple instances are depicted. The front elevation view is shown in the context of individual axes 302 having a longitudinal direction 304, a lateral direction 306, and a vertical (or z) direction 308. The individual axes 302, or reference axes, are orthogonal in configuration. The longitudinal direction 304 is depicted in FIG. 3A as emerging out of and perpendicular to a plane of the illustration (i.e., directed towards the viewer).

The slice member 300 includes a plurality of strips 310 bonded together using a first series of spaced bonds 318 and a second series of spaced bonds 320. The first series of spaced bonds 318 and the second series of spaced bonds 320 are aligned substantially parallel to a longitudinal axis of the unexpanded honeycomb structure (not shown), which is coincident with the longitudinal direction 304. The first series of spaced bonds 318 and the second series of spaced bonds 320 alternate between vertically adjacent strips 316. A first vertical plane 334, substantially parallel to the longitudinal axis of the unexpanded honeycomb structure, or longitudinal direction 304, passes through a first column of nodes 338 in the first series of spaced bonds 318. The first column of nodes 338 corresponds to a first column unexpanded honeycomb cells in the unexpanded honeycomb structure. A second vertical plane 336, substantially parallel to the first vertical plane 334 and displaced laterally therefrom, passes through a second column of nodes 340 in the second series of spaced bonds 320. The second column of nodes 340 corresponds to a second column of unexpanded honeycomb cells in the unexpanded honeycomb structure.

As shown schematically in FIG. 3A, dimensions of the strips 316, the first series of spaced bonds 318, and the second series of spaced bonds 320 have been selected to improve clarity (e.g., a thickness of the first series of space bonds 318, a length of the strips 316, etc.). Such selection is not intended as limiting. For example, and without limitation, the first series of spaced bonds 318 and the second series of spaced bonds 320 typically have thicknesses sufficiently thin to allow individual strips 316 in the plurality of strips 310 to contact one another.

To fabricate a pleated substrate (see 348 in FIG. 3B) from the slice member 300, a first cut is made through the slice member 300 in the first vertical plane 334. A second cut follows in the second vertical plane 336. By combining the first cut and the second cut, a slice section is produced. The slice section can then be stretched along an expansion direction to form the pleated substrate 348. In FIG. 3A, the expansion direction is parallel to the vertical (or z) direction 308. FIG. 3B presents a front elevation view of a pleated substrate 348 (also labeled 342 in some places) fabricated from the slice member 300 of FIG. 3A, according to an illustrative embodiment. The pleated substrate 348 has been stretched to a predetermined length that helps to select a pleat density or number of pleats per unit length.

It will be appreciated that a position of the first vertical plane 334 within the first column of nodes 338 and a position of the second vertical plane 336 within the second column of nodes 340 controls a pleat profile of the pleated substrate 342 (see FIG. 3A). For example, and without limitation, the first vertical plane 334 and second vertical plane 336 can be positioned such that a distance therebetween is minimized. Upon expansion, the slice section would then exhibit virtually no "fin" structure. In contrast, if the distance between the first vertical plane 334 and the second vertical plane 336 were maximized, the slice section would exhibit substantial "fin" structure. Accordingly, FIG. 3B presents only one of many possible pleat profiles for the pleated substrate 342. A width of the first cut and a width of a second cut (e.g., a kerf) may also influence the pleat profile. In some embodiments, the second cut may be made along a vertical plane in the unbounded region 346 up to a third vertical plane 347; this alternative cut would fall between the region of bonding 218 and region of bonding 220 in FIG. 2C.

During fabrication of the pleated substrate 342, the first vertical plane 334 and the second vertical plane 336 stay within boundaries defined by, respectfully, the first column of nodes 338 and the second column of nodes 340. Otherwise, undesired or incomplete pleat profiles would result. For example, and without limitation, if the first vertical plane 334 and the second vertical plane 336 were to enter an unbonded region 342 interior to the first column of nodes 338 and the second column of nodes 340, the slice section would lose continuity and comprise, instead, of a plurality of detached pieces. Similarly, if the first vertical plane 334 and the second vertical plane 336 were to enter unbonded regions 344, 346 adjacent the first column of nodes 338 and the second column of nodes 340 (but not shared in common), the slice section would contain a continuous sequence of honeycomb cells upon expansion.

Now referring primarily to FIG. 3B, the pleated substrate 348 includes a plurality of pleat strips 350 aligned in one respect substantially parallel to a common pleat axis. The common pleat axis in FIG. 3B runs parallel to "folds" in the pleated substrate 348, or parallel to the longitudinal direction 304. Each pleat strip has a first edge 352 and a second edge 354. Surfaces proximate the first edge 352 and the second edge 354 of each pleat strip are bonded so as to form an alternating sequence of peaks 356 and valleys 358. In FIG. 3B, the peaks 356 are bonded together by portions from the first series of spaced bonds 318 while the valleys 358 are bonded together by portions from the second series of spaced bonds 320. However, the peaks 356 and valleys 358 need not be associated with any particular series of spaced bonds. The pleated substrate 348 also has a pleat height 360, which is influenced by the predetermined length (i.e., a degree of stretching in direction 308). Any "fin" structure 362 in the alternating sequence of peaks 356 and valleys 358 may also influence the pleat height 360. Thus, the position of first vertical plane 334 and the second vertical plane 336 can be used to influence the pleat height 360. Other parameters are possible. The pleated substrate 348 is typically coated, in full or in portion, by a photocatalytic material to form a pleated insert.

In some embodiments, the pleated substrate 348 is derived from a slice member having a honeycomb cell size of approximately 1 inch when expanded. (The honeycomb cell size is defined by those skilled in the art as a distance between opposing "flats" or sides when a honeycomb cell assumes a virtually-ideal, hexagonal shape.) In these embodiments, the pleat substrate 348 also has a pleat density of approximately 1 pleat per inch and a pleat height of approximately 0.875 to 1 inches. In further embodiments, the pleated substrate 348 has a pleat width of approximately 1.75 inches. The pleat width typically corresponds to a width of the slice member. These dimensions are for purposes of illustration only and are not meant to be limiting.

Figure 4A:
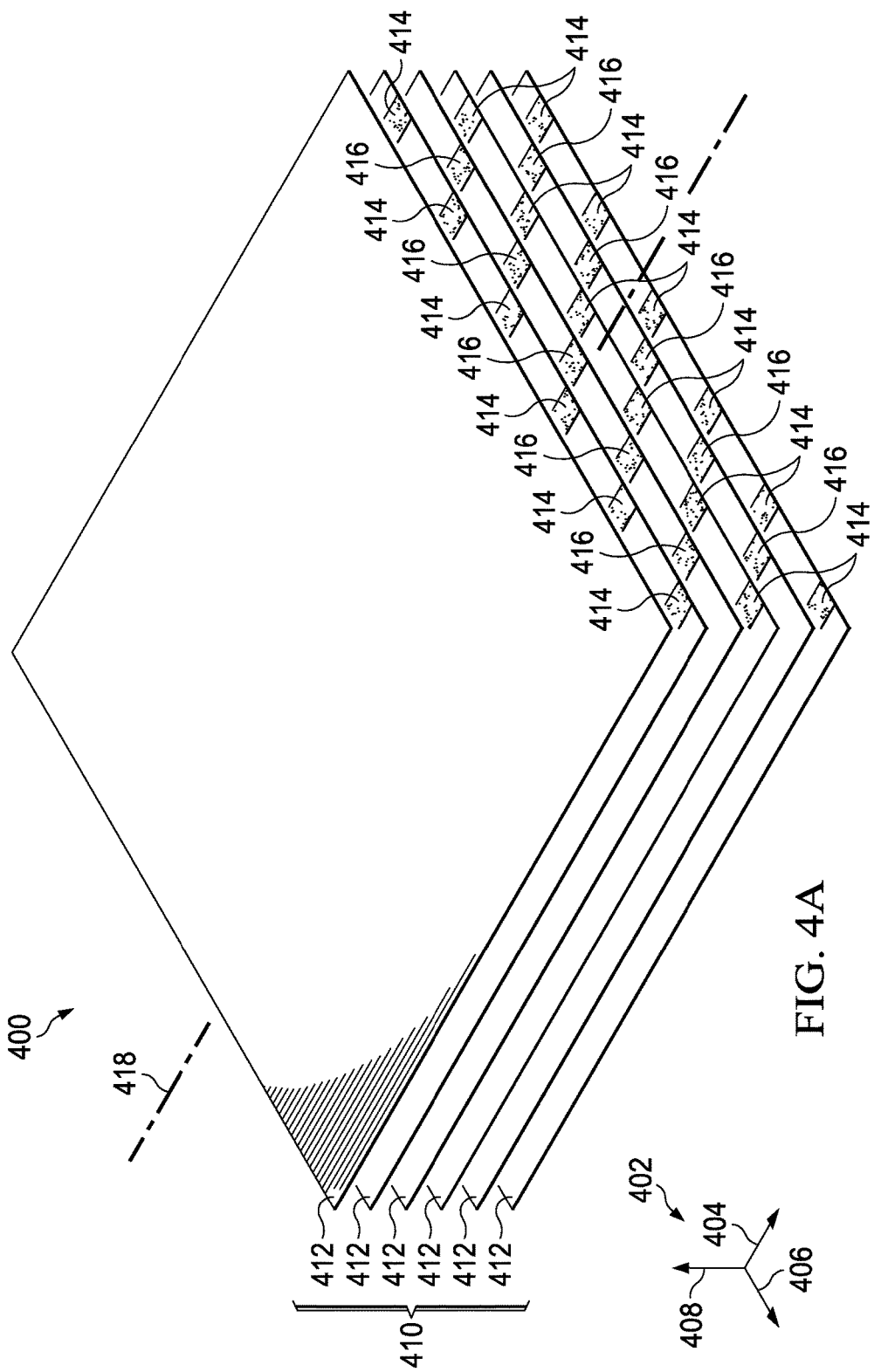
FIG. 4A is a exploded, perspective view of a preform having an unexpanded honeycomb structure, according to an illustrative embodiment.

Now referring primarily to FIG. 4A, an exploded perspective view is presented of a preform 400 having an unexpanded honeycomb structure. The exploded perspective view is shown in the context of individual axes 402 having a longitudinal direction 404, a lateral direction 406, and a vertical direction 408. The individual axes 402, or reference axes, are orthogonal in configuration. The preform 400 includes a plurality of sheets 410 arranged in a stack. Individual sheets 412 in the plurality of sheets 410 are shown with their corresponding regions of bonding 414, 416, which are aligned substantially parallel to the longitudinal direction 404. The longitudinal direction 404 coincides with a longitudinal axis 418 of the unexpanded honeycomb structure. Such regions of bonding 414, 416 enable the preform 400, upon expansion, to assume a preform structure having a honeycomb cross-section.

The regions of bonding 414, 416 include a first series of spaced longitudinal bonds 414 and a second series of spaced longitudinal bonds 416. Relative to the first series of spaced longitudinal bonds 414, the second series of spaced longitudinal bonds 416 is displaced laterally, i.e., along the lateral direction 406. Adjacent sheets 412 are alternately joined by the first series of spaced longitudinal bonds 414 and the second series of spaced longitudinal bonds 416. The first series of spaced longitudinal bonds 414 and the second series of spaced longitudinal bonds 416 may be formed by soldering, brazing, welding, ultrasonic welding, gluing, epoxying, adhesive bonding, or any other means of joining surfaces or bodies.

Figure 4B:
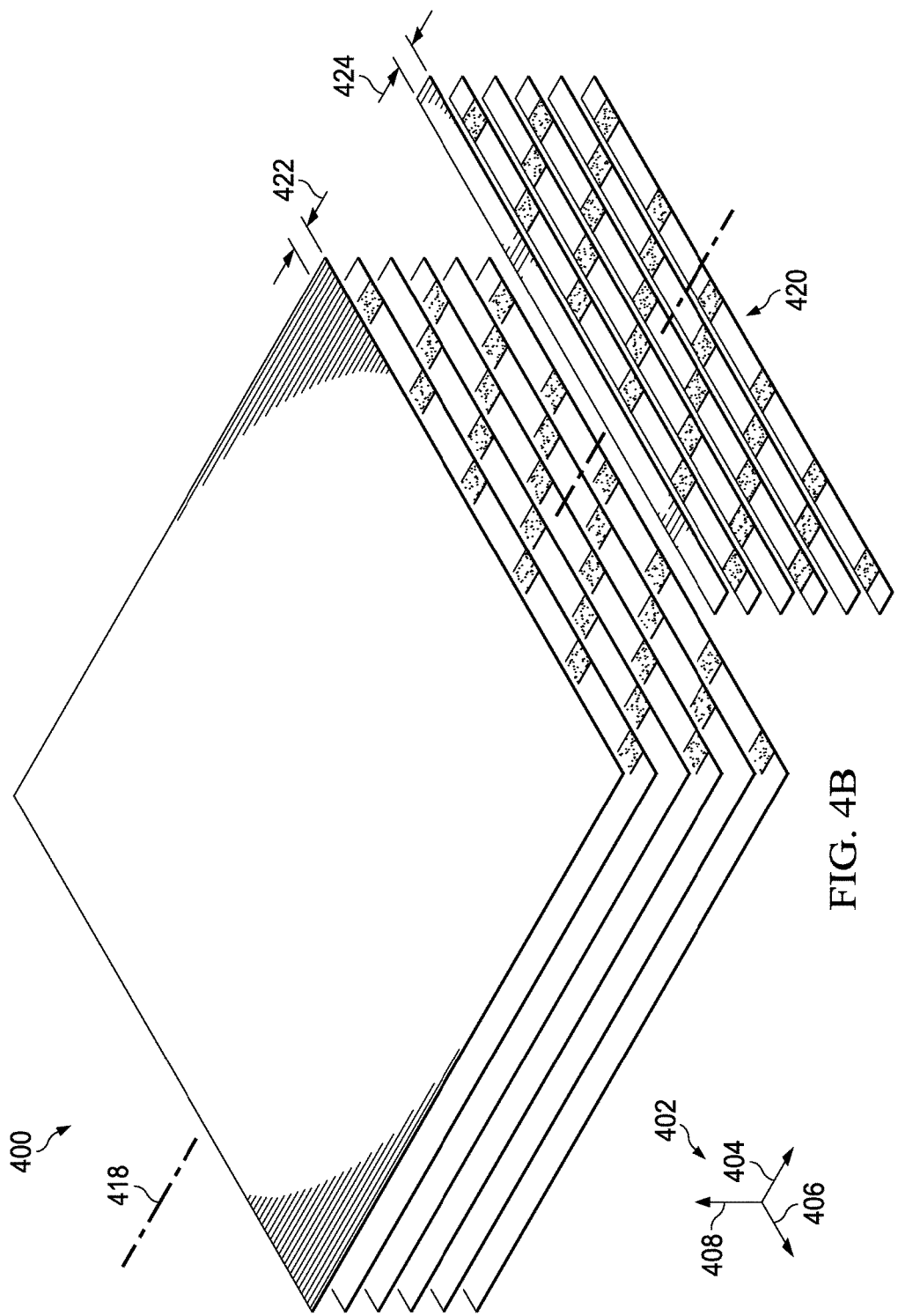
FIG. 4B is an exploded, perspective view of a preform cut to produce a slice member, according to an illustrative embodiment.

A slice member may be produced by cutting through the preform 400, and more specifically, cutting substantially perpendicular to the longitudinal axis 418 of the unexpanded honeycomb structure. FIG. 4B presents an exploded perspective view of a preform 400 cut to produce a slice member 420, according to an illustrative embodiment. The slice member 420 of FIG. 4B is analogous to the slice member 200 described in relation to FIGS. 2A-2C. During cutting, a depth of cut 422 is selected to control a width 424 of the slice member 420. Cuts may be made along the longitudinal axis 418 of the unexpanded honeycomb structure at multiple locations to produce multiple slice members 420 as needed.

According to an illustrative embodiment, a method for fabricating a pleated substrate for use in an HVAC catalytic air filter from a slice member having an unexpanded honeycomb structure includes the step of making a first cut through the slice member. The first cut is substantially parallel to a longitudinal axis of the unexpanded honeycomb structure and in a vertical plane. Moreover, the first cut is through a first column of unexpanded honeycomb cells in the unexpanded honeycomb structure. The method also includes the step of making a second cut through the slice member, thereby producing a slice section. The second cut is laterally displaced from the first cut and substantially parallel thereto. In addition, the second cut is through a second column of unexpanded honeycomb cells in the unexpanded honeycomb structure. The second column of unexpanded honeycomb cells is adjacent the first column of unexpanded honeycomb cells. The method involves the step of stretching the slice section in an expansion direction to a predetermined length in order to form the pleated substrate.

In some embodiments, the method further comprises the step of coating the pleated substrate with a photocatalytic material to form a pleated insert. In some embodiments, the method further comprises the step of coating the pleated substrate with a photocatalytic material to form a pleated insert and the step of disposing the pleated insert into a housing having a source of electromagnetic radiation and configured to purify air. In some embodiments, the photocatalytic material includes a titanium dioxide material.

In some embodiments, the slice member is comprised of a plurality of strips arranged in a stack. In such embodiments, adjacent strips in the plurality of strips are alternately joined by a first series of spaced bonds and a second series of spaced bonds. The first series of spaced bonds and the second series of spaced bonds are aligned substantially parallel to the longitudinal axis of the unexpanded honeycomb structure. Moreover, the second series of spaced bonds is displaced laterally relative to the first series of spaced bonds so that the slice member, upon expansion, assumes a slice member structure having a honeycomb cross-section.

In some embodiments, the method further comprises the step of producing the slice member by cutting through a preform having the unexpanded honeycomb structure. In these embodiments, the cutting is substantially perpendicular to the longitudinal axis of the unexpanded honeycomb structure. Moreover, preform is comprised of a plurality of sheets arranged in a stack. Adjacent sheets in the plurality of sheets are alternately joined by a first series of spaced longitudinal bonds and a second series of spaced longitudinal bonds. The first series of spaced longitudinal bonds and the second series of spaced longitudinal bonds are aligned substantially parallel to the longitudinal axis of the unexpanded honeycomb structure. In addition, the second series of spaced longitudinal bonds is displaced laterally relative to the first series of spaced longitudinal bonds so that the preform, upon expansion, assumes a preform structure having the honeycomb cross-section.

In some embodiments, the method further comprises the step of alternately making the first cut and the second cut along the slice member to produce a plurality of slice sections. In these embodiments, each slice section of the plurality of slice sections is stretched in the expansion direction to a corresponding predetermined length.

Figure 5:
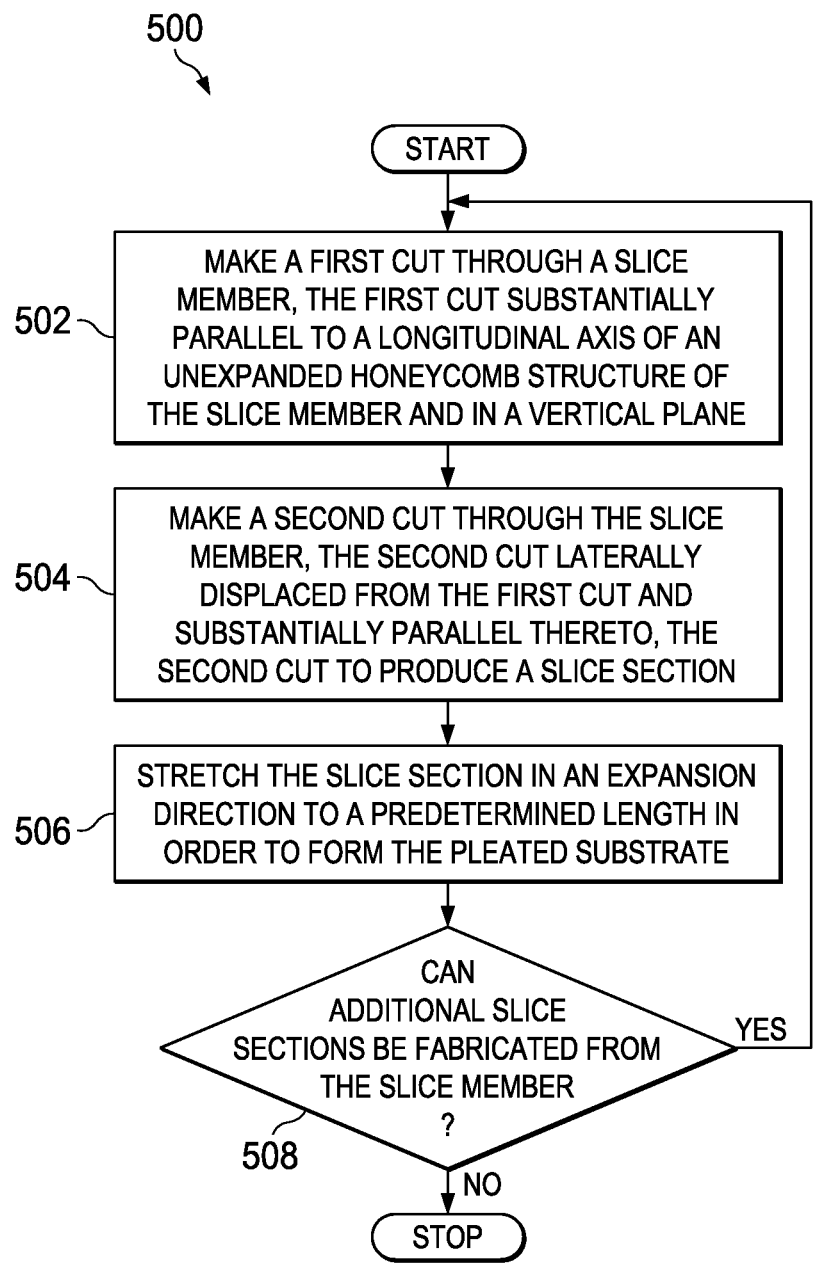
FIG. 5 is flow chart of an illustrative method for fabricating a pleated substrate for use in an HVAC catalytic air filter from a slice member having an unexpanded honeycomb structure.

Now referring primarily to FIG. 5, a flow chart is presented of an illustrative method 500 for fabricating a pleated substrate for use in an HVAC catalytic air filter. The pleated substrate is fabricated from a slice member having an unexpanded honeycomb structure. The method includes the step 502 of making a first cut through the slice member. The first cut is substantially parallel to a longitudinal axis of the unexpanded honeycomb structure and in a vertical plane. Moreover, the first cut is through a first column of unexpanded honeycomb cells in the unexpanded honeycomb structure. The method also includes the step 502 of making a second cut through the slice member to produce a slice section. The second cut is laterally displaced from the first cut and substantially parallel thereto. In addition, the second cut is through a second column of unexpanded honeycomb cells in the unexpanded honeycomb structure. The second column of unexpanded honeycomb cells is adjacent the first column of unexpanded honeycomb cells. The method involves the step 506 of stretching the slice section in an expansion direction to a predetermined length in order to form the pleated substrate.

The step 506 of stretching the slice section may be followed by a decision, represented by interrogatory 508, of determining if additional slice sections can be fabricated from the slice member. If additional slice sections can be fabricated, the method 500 returns to the step 502 of making a first cut. However, when iterated, the first cut is positioned at a new location on the slice member, typically within an adjacent, uncut column of nodes within the first series of spaced bonds 318. If additional slices cannot be fabricated, the method 500 stops. It should be appreciated that in some embodiments additional slice sections may be made with only one more cut and thus could return in the flow diagram between steps 502 and 504.

According to an illustrative embodiment, a method for fabricating a pleated substrate from a slice member having an unexpanded honeycomb structure includes the step of making a first cut through the slice member. The first cut is substantially parallel to a longitudinal axis of the unexpanded honeycomb structure and in a vertical plane. Moreover, the first cut is exclusively through a first column of unexpanded honeycomb cells in the unexpanded honeycomb structure. The method also includes the step of making a second cut through the slice member, thereby producing a slice section. The second cut is laterally displaced from the first cut and substantially parallel thereto. In addition, the second cut is exclusively through a second column of unexpanded honeycomb cells in the unexpanded honeycomb structure. The second column of unexpanded honeycomb cells is adjacent the first column of unexpanded honeycomb cells. The method involves the step of stretching the slice section in an expansion direction to a predetermined length in order to form the pleated substrate.

In some embodiments, the method further comprises the step of coating the pleated substrate with a photocatalytic material to form a pleated insert. In some embodiments, the method further comprises the step of coating the pleated substrate with a photocatalytic material to form a pleated insert and the step of disposing the pleated insert into a housing having a source of electromagnetic radiation and configured to purify air.

The pleated substrate may be coupled to a cartridge housing. The cartridge housing may be inserted into a filter-housing unit. The filter-housing unit may be introduced into a portion of an HVAC system. In other applications, the pleated substrate might be used in applications requiring a high surface area in small package.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order or simultaneous where appropriate. Where appropriate, aspects of any of the examples described above may be combined with aspects of any of the other examples described to form further examples having comparable or different properties and addressing the same or different problems.

It will be understood that the above description of the embodiments is given by way of example only and that various modifications may be made by those skilled in the art. The above specification, examples, and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

In the detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the scope of the invention. To avoid detail not necessary to enable those skilled in the art to practice the embodiments described herein, the description may omit certain information known to those skilled in the art. The detailed description above is, therefore, not to be taken in a limiting sense, and the scope of the illustrative embodiments is defined only by the appended claims.

In the drawings and description herein, like parts are typically marked throughout the specification and drawings with the same reference numerals or coordinated numerals. The drawing figures are not necessarily to scale. Certain features of the illustrative embodiments may be shown exaggerated in scale or in somewhat schematic form and some details of conventional elements may not be shown in the interest of clarity and conciseness.

Unless otherwise specified, any use of any form of the terms "connect," "engage," "couple," "attach," or any other term describing an interaction between elements is not meant to limit the interaction to direct interaction between the elements and may also include indirect interaction between the elements described. In the following discussion and in the claims, the terms "including" and "comprising" are used in an open-ended fashion, and thus should be interpreted to mean "including, but not limited to". Unless otherwise indicated, as used throughout this document, "or" does not require mutual exclusivity.

I claim:

1. A system for purifying air using electromagnetic radiation, the system comprising:
   a cartridge housing;
   a source of electromagnetic radiation disposed within the cartridge housing;
   at least one pleated insert disposed within the cartridge housing and proximate the source of electromagnetic radiation, the at least one pleated insert comprising:
   a plurality of pleat strips aligned substantially parallel to a common pleat axis, each pleat strip having a first edge and a second edge, the first edge and the second edge reside on opposite sides of each pleat strip, and wherein surfaces proximate the first edge and the second edge of each pleat strip are bonded to adjacent pleat strips so as to form an alternating sequence of peaks and valleys having openings between adjacent peaks such that, in an elevation view, the plurality of pleat strips form a zig-zag pattern; and wherein a photocatalytic material coats at least a portion of the pleated insert; and wherein the cartridge housing is configured to guide air to the at least one pleated insert.

2. The system of claim 1, wherein the at least one pleated insert comprises two pleated inserts, the two pleated inserts positioned opposite each other so as to straddle the source of electromagnetic radiation.

3. The system of claim 1, wherein the source of electromagnetic radiation is configured to extend along an expansion length of the at least one pleated insert.

4. The system of claim 1, wherein the source of electromagnetic radiation is configured to emit ultraviolet radiation in a UVA frequency spectrum, a UVB frequency spectrum, a UVC frequency spectrum, or any combination thereof.

5. The system of claim 1, wherein the source of electromagnetic radiation is configured to extend along a length of the at least one pleated insert and wherein the source of electromagnetic radiation is configured to emit ultraviolet radiation in a UVA frequency spectrum, a UVB frequency spectrum, a UVC frequency spectrum, or any combination thereof.

6. The system of claim 1, wherein the plurality of pleated strips are bonded using an adhesive.

7. The system of claim 1, wherein the plurality of pleated strips comprises an aluminum material.

8. The system of claim 1, wherein the plurality of pleated strips comprises a kraft paper material.

9. The system of claim 1, wherein the plurality of pleated strips comprises an aramid material.

10. The system of claim 1, wherein the photocatalytic material comprises a titanium oxide material.

* * * * *